Figure 1:
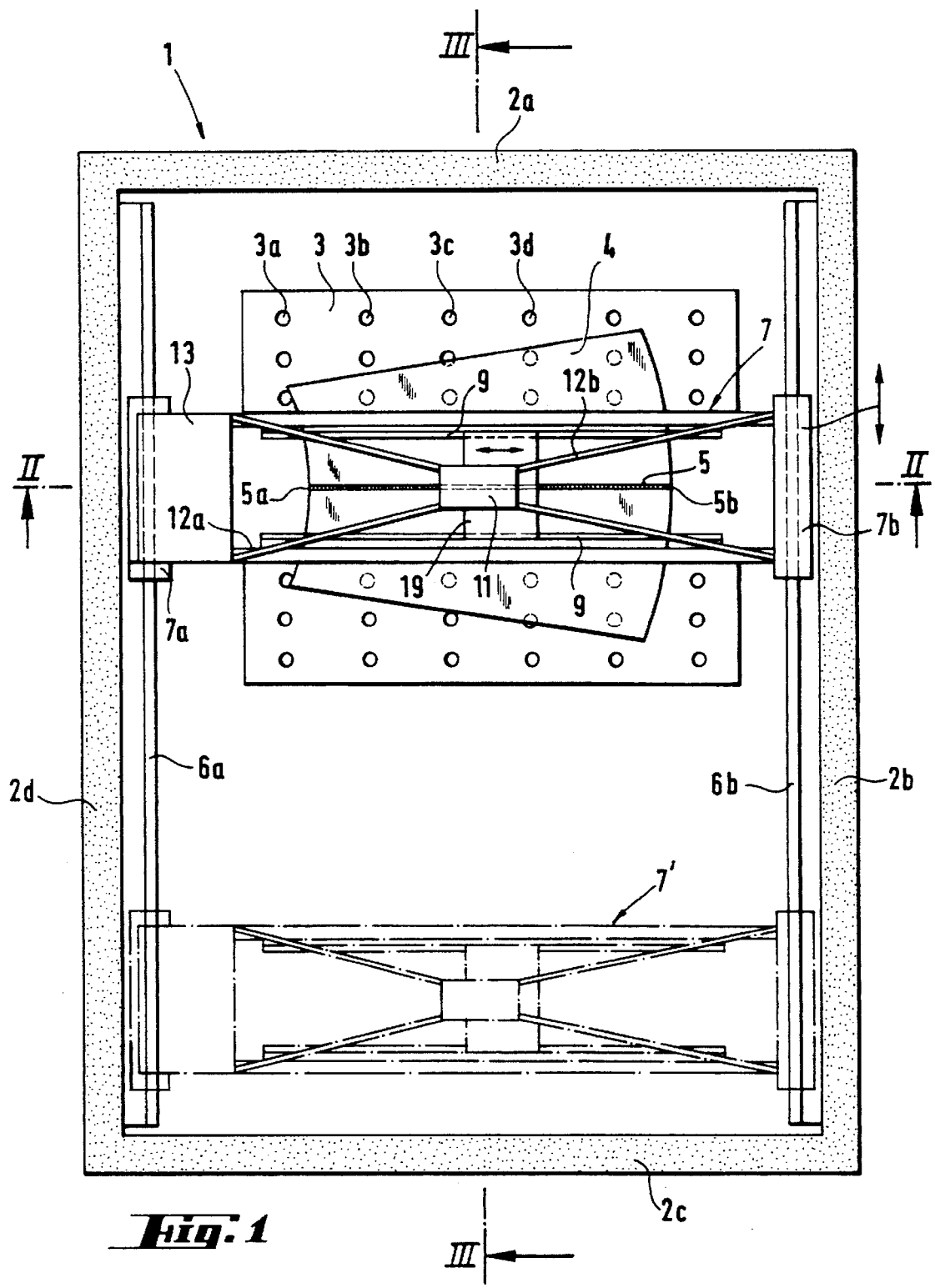

United States Patent [19]
Gustafsson et al.

[11] Patent Number: 5,648,619
[45] Date of Patent: Jul. 15, 1997

[54] ARRANGEMENT FOR INSPECTION OF WELDED PLATE SECTIONS

[75] Inventors: Jukka Gustafsson, Mynämäki; Jari Salmi, Raisio; Heikki Laiho, Turku, all of Finland

[73] Assignee: Kvaerner Masa-Yards Oy, Helsinki, Finland

[21] Appl. No.: 530,082

[22] Filed: Sep. 19, 1995

[30] Foreign Application Priority Data

Oct. 19, 1994 [FI] Finland ................... 944895

[51] Int. Cl.$^6$ ................................................. G01B 11/24
[52] U.S. Cl. ................................................. 73/865.8
[58] Field of Search .................. 73/865.8, 865.9; 356/376, 377; 378/55, 58–60, 68, 177, 180, 181, 195–198, 208

[56] References Cited

U.S. PATENT DOCUMENTS

| | | | |
|---|---|---|---|
| 2,370,163 | 2/1945 | Hare | 378/58 |
| 4,209,252 | 6/1980 | Arditty et al. | 356/377 |
| 4,694,479 | 9/1987 | Bácskai et al. | |
| 5,237,598 | 8/1993 | Albert. | |
| 5,446,549 | 8/1995 | Mazumder et al. | |
| 5,467,289 | 11/1995 | Abe et al. | 356/377 |

FOREIGN PATENT DOCUMENTS

| | | | |
|---|---|---|---|
| 0209307 | 8/1989 | Japan | 356/376 |
| 2211708 | 7/1989 | United Kingdom | 378/58 |
| 2275164 | 8/1994 | United Kingdom. | |

*Primary Examiner*—Robert Raevis
*Attorney, Agent, or Firm*—Smith-Hill and Bedell

[57] ABSTRACT

An arrangement for inspecting arcuate plate assemblies of aluminum with a thickness of at least 20 mm, intended for the manufacturing of large spherical LNG-tanks or the like includes a fastening jig (3) for plate assemblies (4) to be inspected, and inspection and measuring means allowing, in a single fixation of a plate assembly (4) in the fastening jig (3), inspection of one or several weld joints (5). Measuring of the arcuate shape of a shape of the plate assembly (4), whereby, for the inspection of the weld joint(s) includes at one side of the plate assembly (4), a first carriage (19) movable along a first rail system (9), which carriage (19) is provided with a radiation source (20) for X-ray material inspection and, at the other side of the plate assembly (4) and a second carriage (14) movable along a second rail system (8), which the second carriage (14) is provided with a picture amplifier (16) and a video camera (17) for X-ray inspection. For shape inspection of the plate assembly (4), a laser measuring device (11) is located at a considerable distance from the plate assembly (4).

18 Claims, 4 Drawing Sheets

ARRANGEMENT FOR INSPECTION OF WELDED PLATE SECTIONS

The invention relates to an arrangement for inspecting welded plate assemblies bent to an arcuate form and to a LNG-tank or the like.

When tanks for transport and/or storing of liquefied natural gas (LNG) are made, large and relatively thick aluminum plates are welded together and they are shaped to portions of a spherical surface, which portions are then joined to other spherical portions to form the tank. The diameter of a spherical tank is usually more than 20 m, even more than 40 m. The welded plate assemblies brought together to form the tank are extremely large and one must also start with plate blanks as large as possible for minimizing the dominant welding costs. The quality requirements for the weld joints are very high. The welded plate assemblies must also have exact shape and dimension, otherwise an acceptable final result is not obtainable.

The weld joints are inspected by several methods for revealing possible weld defects. A basic method is X-ray photographing. An X-ray film cassette is placed at one side of the weld and at the other side there is an X-ray source, whereby X-ray pictures of the weld are obtainable. This method is applicable only to short weld portions, normally less than half a meter. X-ray photographing welds of 5 to 10 meters of length takes too long and includes work hazards. Weld defects are revealed only after the X-ray films have been developed. It might then be difficult to spot the exact place of each weld defect.

Since the LNG-tank weld joints must be inspected over their whole length, one would need thousands of X-ray films for one tank, which take up much space, because the size of an X-ray film generally used is 100×480 mm.

For inspection of the shape of a welded plate assembly a template is placed at the work-piece at different points and in different directions. This makes it possible to check the shape of the edge of a plate, but not its exact location in space. It is also difficult and expensive to manufacture and use large and exact templates. Templates of more than 10 meters in length cannot conveniently be used at all.

The object of the invention is to essentially speed up and automate the inspection of weld joints and of the shape of welded plate assemblies, and to decrease the risk of error in the inspection work and in the analysis of the work. Another object is to improve the safety of the inspection work and to decrease essentially the space required for inspection equipment and film material.

An arrangement according to the invention is particularly suitable for the inspection of large arcuate aluminum plate assemblies with a thickness of at least 20 mm. The reinforcement is removed by milling and the surface is usually finished by grinding. The initial steps of forming large plate assemblies are described in EP - A - 570212.

An arcuate plate assembly has one convex side and one concave side. According to the invention the inspection site includes an X-ray equipment and laser measuring devices for shape inspection. The surroundings of the inspection site are to be protected from the X-rays used in the inspection. There is further a fastening jig, where plate assemblies can be inspected with respect to the weld joints as well as to their shape.

For the inspection of a plate assembly there is a first carriage movable along a first rail system at the one side of the plate assembly. The first carriage has an X-ray source. At the opposite side of the plate assembly there is a second rail system along which a second movable carriage with a picture amplifier and a video camera is able to move. For shape inspection there are laser measuring devices at one side of the plate assembly preferably located in a direction perpendicularly to the plate at its center point. It is of advantage to carry out the inspection and the measuring by remote control of the carriages. All inspections may be accomplished without moving the plate assembly, which simplifies the inspection process. The inspections may even be carried out simultaneously, but it is preferred that they be carried out one after another, so that the inspections do not disturb each other in any way.

The laser measuring devices and the X-ray source are preferably at the convex side of the plate assembly. This equipment and the rails of its rail system may then easily be moved aside from the plate assembly after completing the inspection work, so that the plate assembly can easily be removed from the inspection site. It is of advantage that the radiation source is above and the picture amplifier and the video camera are under the plate assembly. If X-rays are emitted in a downwards direction, a spreading of the radiation to the surroundings is easily prevented. Additionally, the plates to be inspected can easily be moved in to and out from the inspection site, provided that the plates are to be inspected mainly in the horizontal position.

The movements of the carriages are preferably synchronized so that the inspection devices, the X-ray source, the picture amplifier and the video camera during the inspection process automatically take such positions relative to each other that the picture amplifier and the video camera can take the required pictures. Normally, the carriages are displaced about 10 cm. when moving from one inspection point to another.

The inspection may be followed from an inspection room and defects may be detected immediately. The inspection room is protected from the radiation. There the inspection results are recorded. When defects are detected, the inspector records the position of the defect, after which the inspection devices by remote control are moved to the following inspection position.

In a preferred embodiment both the first rail system and the second rail system follow the shape of the plate assembly at the inspection area. The inspection devices are thus in all inspection points, approximately at the same distance from the surface of the plate assembly. It is of advantage that the inspection devices operate in all the inspection points, approximately perpendicularly to the plate assembly. Thereby the function of the inspection devices is best controlled.

It is of advantage, in shape inspection of a plate assembly, that the laser measuring device is at a distance of at least 5 meters, preferably more than 9 meters from the plate assembly. The laser measuring device has a so called three-dimensional laser measuring head, which is arranged far enough and in a direction that preferably is approximately perpendicular to the plate assembly at its center point. When measuring the shape of a plate assembly from its convex side the angle between any normal of the plate assembly and the measuring direction remains within acceptable limits because of the great distance of the laser measuring head from the plate assembly.

The inspection devices at the side of the plate assembly that is opposite to the fastening jig, preferably the convex side of the plate assembly are movable farther away from the fastening jig, so that the plate assembly may easily be replaced by another one. The inspection devices may, in particular at the convex side of the plate assembly, be placed on a carriage that moves supported by a third rail system, the rails of which are laterally outside the fastening jig. Since the rails of the third rail system are in this case so far from each other, at both sides of the fastening jig, the arrangement becomes easily firm and rigid.

The shape inspection data of the plate assembly and the inspection data of the weld joint are preferably recorded directly on a compact disc. Compared to the conventional X-ray film cassette technique, the time required for taking the pictures is almost the same, but no film developing is necessary according to the invention. Thus, transport of X-ray films to and from the inspection site is not necessary, and the storage space required for inspection recordings is reduced by approximately 98% compared to the known art. Also safety at work is improved, since manual handling of X-ray film cassettes at a possibly labyrinthian inspection site is not needed. The whole inspection work may be accomplished by a remote-controlled process, in most cases totally automatically. If necessary, it is easy to later check the inspection data, even by means of the same devices.

The invention also relates a large spherical LNG-tank or the like with a diameter of more than 20 meters and made by welding of aluminum plates with a thickness of at least 20 mm, in which the plate assemblies have been inspected by the means disclosed above.

Figure 2:
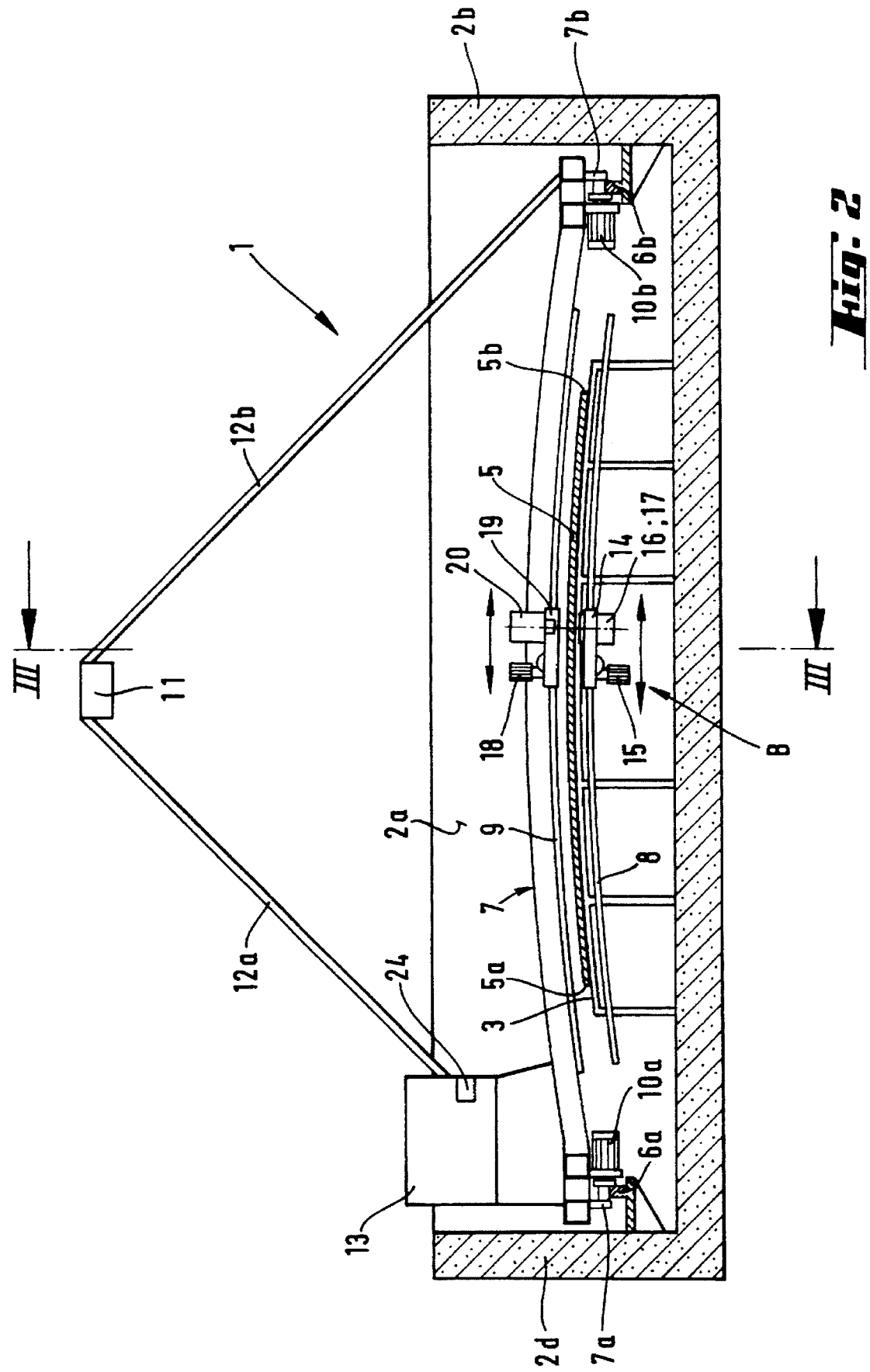
Figure 3:
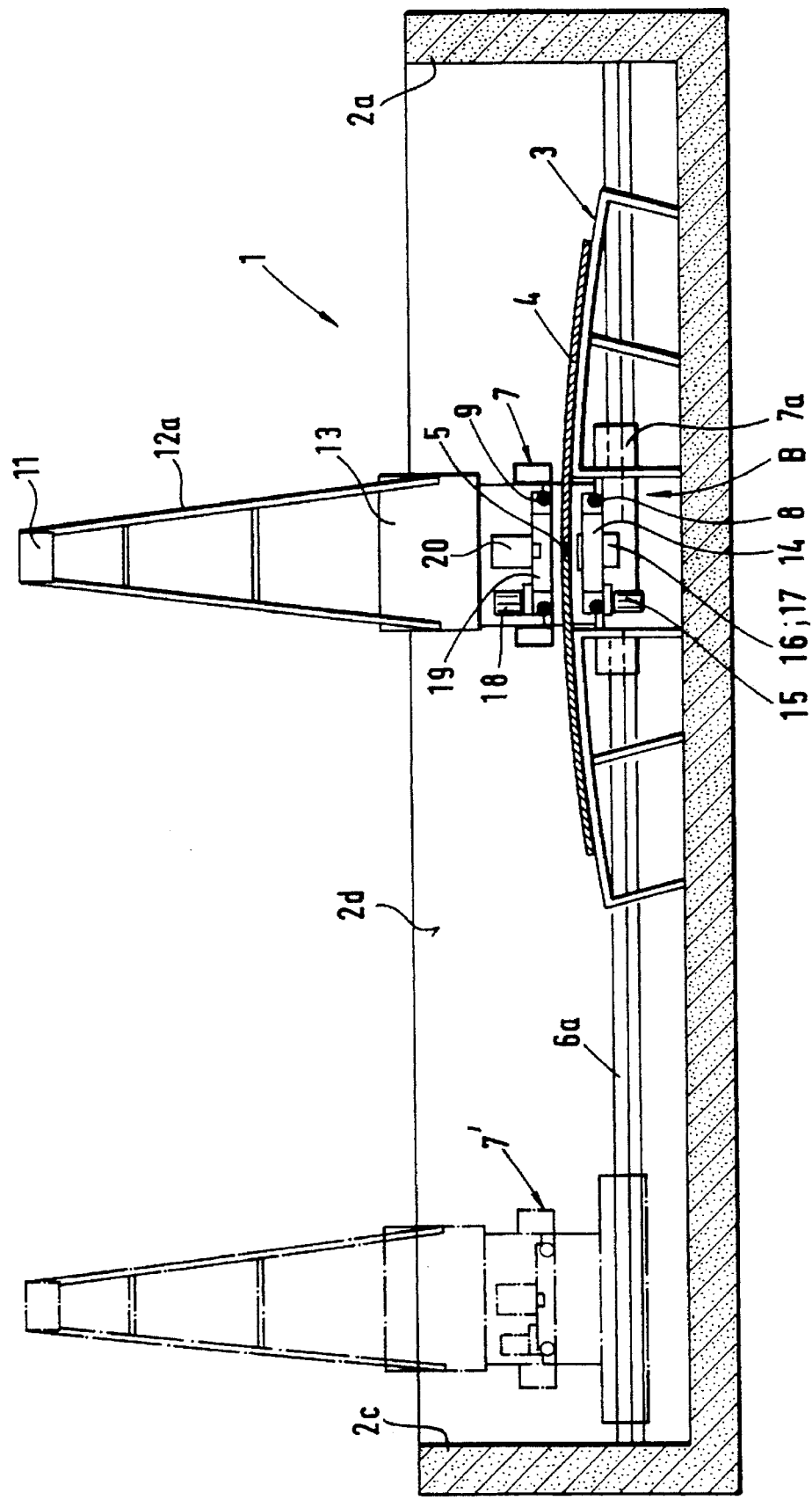
Figure 4:
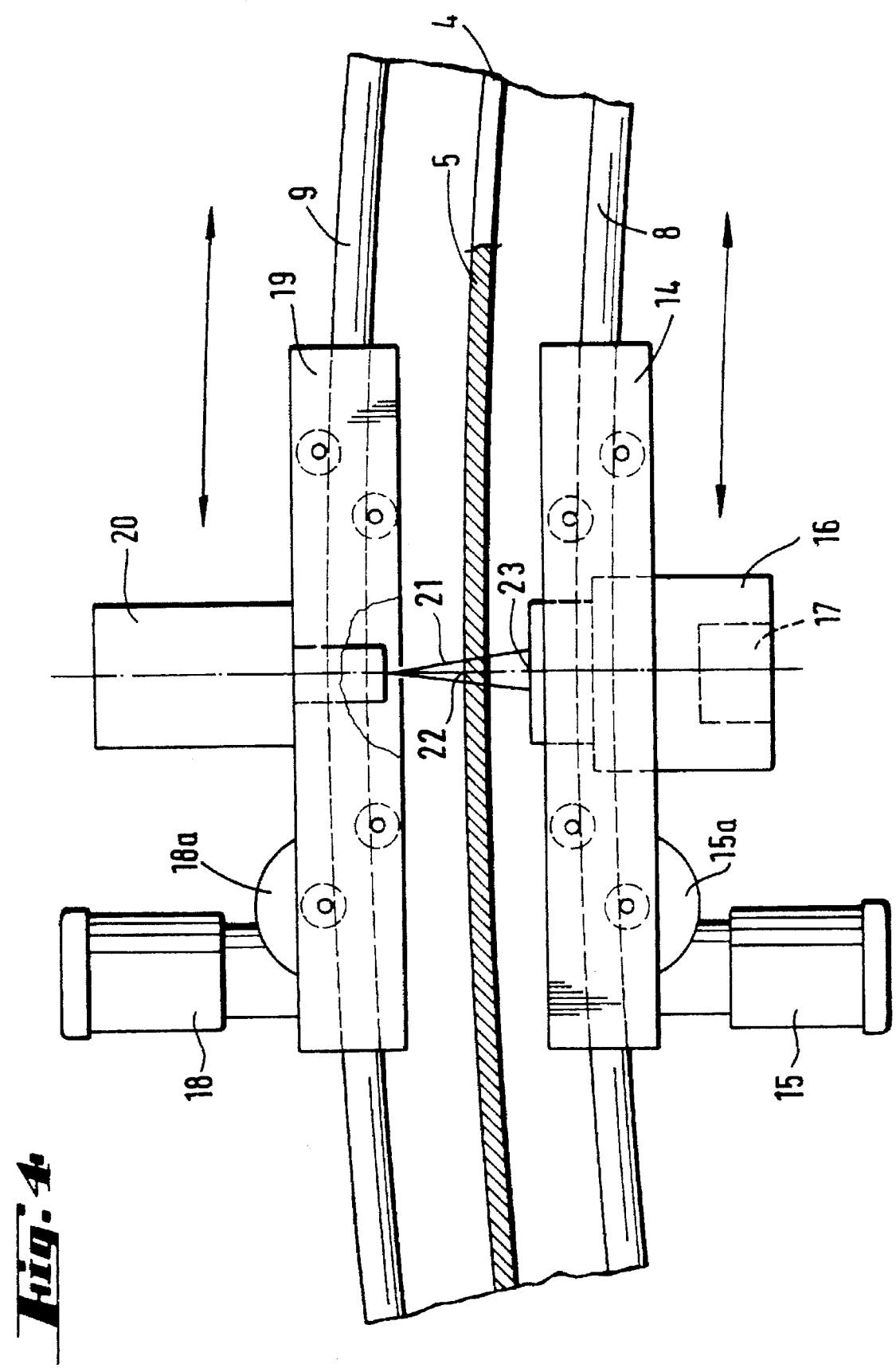

The invention will now be described more in detail with reference to the accompanying drawings, in which FIG. 1 schematically shows a top view of an inspection site according to the invention, FIG. 2 schematically shows cross-section II—II of FIG. 1, FIG. 3 schematically shows section III—III of FIG. 2, FIG. 4 shows details of the inspection devices schematically shown in FIG. 2, FIG. 5 is a perspective view of a large spherical tank.

In the drawings, 1 indicates an inspection site surrounded by radiation protection walls 2a, 2b, 2c and 2d. There is a fastening jig 3 with support points 3a, 3b, 3c, 3d, etc. including suction fastening devices (not shown) or other devices for fixing a plate assembly 4. A weld joint 5 of the plate assembly to be inspected is placed between the points 5a and 5b. There are two rails 6a and 6b one at each side of the fastening jig 3. The weld joint 5a–5b to be inspected is approximately perpendicularly to the rails 6a and 6b and approximately in the center area of the fastening jig 3. A carriage 7, carried by a wheel arrangement, runs driven by carriage drive motors 10a and 10b shown in FIG. 2 along rails 6a and 6b, carried by wheel arrangements 7a and 7b. When the carriage 7 is moved away from the fastening jig area it may have the position 7'.

FIGS. 2 and 3 show a second rail system 8 with rails and their supporting structures is located under the center area of the fastening jig 3 at its central area. There is another rail system 9 with rails and support structure above the plate assembly 4. B indicates weld joint inspection devices. More than 9 m above the plate assembly there is a laser inspection device 11 for shape inspection. It has a measurement accuracy of about ±1 mm. It is supported by beams 12a and 12b. The measuring area of the device 11 covers the entire plate assembly. An inspection room 13 protected from X-ray radiation is placed on the carriage 7 aside of the fastening jig 3.

FIG. 4 shows a carriage 14 having an electric drive motor 15 and power transmission devices 15a for driving it along the second rail system 8. The carriage 14 carries a picture amplifier 16 and a video camera 17. On the first rail system 9 above the weld joint 5 of the plate assembly 4 there is a cooperating carriage 19 driven by an electric motor 18 and power transmission devices 18a. The carriage 19 is provided with a radiation source 20 transmitting X-rays 21 passing approximately perpendicularly through the plate assembly 4, mainly at the center point 22 of the X-ray beam. The movements of the carriages 14 and 19 are synchronized so that the center point 23 of the picture amplifier 16 follow the center 22 of the X-ray beam 21.

The inspection of the weld joint 5 is preferably started from one end of the weld joint. The carriages 14 and 19 are moved about 10 cm from one inspection point to another. As an auxiliary device one may use a scale tape made of lead at one side of the inspected weld joint. The inspection data is recorded by devices 24 on compact discs. Normally, an inspector is observing the quality of the weld joint 5 all the time.

The shape inspection of the plate assembly may be accomplished before or after the weld inspection. Stationary checking points (not shown) are arranged in association with the fastening jig 3, by means of which the measuring device 11 is initially calibrated. The desired quantity and position of the measuring points is determined, after which the measuring device 11 measures the actual shape of the surface of the plate assembly 4 and compares it to a theoretical spherical shape.

FIG. 5 illustrates a large spherical tank 30 composed of multiple plate assemblies 4 that have been inspected using the arrangement shown in FIGS. 1–4. The plate assemblies 4 are joined together along lines 31. Only one segment 32 of the tank is shown in solid lines.

The invention is not restricted to the embodiments shown, but several modifications thereof are feasible within the scope of the attached claims.

We claim:

1. An arrangement for inspecting arcuate plate assemblies of aluminum with a thickness of at least 20 mm, for manufacture of large arcuate objects such as LNG tanks, comprising:

a fastening jig for holding a plate assembly that is to be inspected at a predetermined inspection position having first and second opposite sides, a weld inspection means comprising, at the first side of the inspection position, a first rail system, a first carriage mounted on the first rail system for movement therealong, and a radiation source for X-ray material inspection carried by the first carriage, and, at the second side of the inspection position, a second rail system, a second carriage mounted on the second rail system for movement therealong, and an imaging means including a video camera for X-ray inspection carried by the second carriage, and a laser measuring device located at a considerable distance from the predetermined inspection position for measuring the arcuate shape of the plate assembly over substantially its entire area.

2. An arrangement according to claim 1, wherein a plate assembly held by the fastening jig is convex toward the first side of the inspection position and the laser measuring device is at the first side of the inspection position.

3. An arrangement according to claim 1, wherein a plate assembly held by the fastening jig is generally horizontal, and the radiation source is above and the imaging means is below the predetermined inspection position.

4. An arrangement according to claim 1, comprising a means for synchronizing movement of the first and second carriages along the first and second rail systems so that the radiation source and the imaging means are situated relative to each other so that they can cooperate in inspection of the weld.

5. An arrangement according to claim 1, wherein the first rail system and the second rail system follow the shape of the plate assembly at the inspection area of the weld joint.

6. An arrangement according to claim 1, wherein the laser measuring device is located at a distance of at least five meters from the inspection position.

7. An arrangement according to claim 1, wherein the laser measuring device is located at a distance of more than nine meters from the inspection position.

8. An arrangement according to claim 1, wherein the fastening jig has a convex upper surface for receiving a plate assembly that is to be inspected.

9. An arrangement according to claim 1, comprising a pair of rails between which the fastening jig is located and wherein one of said first and second rail systems is mounted on said pair of rails for movement therealong between a first position, in which said one rail system spans the fastening jig, and a second position, in which said one rail system is spaced from the fastening jig to allow a plate assembly to be placed in and removed from the inspection position.

10. An arrangement according to claim 9, wherein the laser measuring device is mounted on said one rail system for movement therewith along the pair of rails.

11. An arrangement according to claim 17, wherein the fastening jig has a convex upper surface for receiving a plate assembly that is to be inspected, and the arrangement further comprises a pair of rails between which the fastening jig is located, the first rail system is mounted on said pair of rails for movement therealong between a first position, in which the first rail system spans the fastening jig, and a second position, in which said one rail system is spaced from the fastening jig to allow a plate assembly to be placed in and removed from the inspection position, and the laser measuring device is mounted on the first rail system for movement therewith along the pair of rails.

12. An arrangement according to claim 1, comprising means for recording weld inspection data and shape measurement data on a compact disc.

13. A method for inspecting an arcuate plate assembly of aluminum with a thickness of at least 20 mm, for manufacture of a large spherical tank, comprising:

securing the arcuate plate assembly in a predetermined inspection position such that there is, at a first side of the plate assembly, a weld inspection means comprising a first rail system, a first carriage mounted on the first rail system for movement therealong, and a radiation source for X-ray material inspection carried by the first carriage, and, at a second side of the plate assembly, a second rail system, a second carriage mounted on the second rail system for movement therealong, and an imaging means including a video camera for X-ray inspection carried by the second carriage, and a laser measuring device is located at a considerable distance from the plate assembly, employing the weld inspection means to inspect a weld in the plate assembly, and, while keeping the plate assembly in its inspection position, employing the laser measuring device for measuring the arcuate shape of the plate assembly over substantially its entire area.

14. A method according to claim 13, comprising moving the first carriage and the second carriage synchronously along the first rail system and the second rail system respectively while employing the weld inspection means to inspect the weld in the plate assembly.

15. A method according to claim 13, wherein the arcuate plate assembly, when secured in the predetermined inspection position, is located between a pair of rails, one of the first and second rail systems is supported by the pair of rails and extends over the arcuate plate assembly and the other of the first and second rail system extends under the arcuate plate assembly, and the method further comprises:

displacing said one rail system along the pair of rails to a location in which it is spaced from the arcuate plate assembly in the inspection position, removing the arcuate plate assembly from the inspection position, securing a second arcuate plate assembly in the predetermined inspection position, and displacing said one rail system along the pair of rails to the position in which it extends over the other rail system.

16. A method according to claim 13, comprising recording weld inspection data and shape measurement data on a compact disc.

17. An arcuate plate assembly that has been inspected by a method according to claim 13.

18. A spherical tank having a diameter of at least about 20 m and composed of arcuate plate assemblies having a thickness of at least about 20 mm, and wherein the plate assemblies have been inspected by a method according to claim 13.

* * * * *